United States Patent [19]

Clouet et al.

[11] Patent Number: 5,200,545
[45] Date of Patent: Apr. 6, 1993

[54] THIURAM DISULPHIDES CONTAINING PHOSPHATE OR PHOSPHONATE FUNCTIONAL GROUPS, THEIR PREPARATION AND THEIR USE IN THE MANUFACTURE OF FIREPROOFING VINYL POLYMERS

[75] Inventors: Gilbert Clouet, La Wantzenau, France; C. P. Reghunadhan Nair, Trivandrum, India

[73] Assignee: Elf Atochem S.A., Paris-La Defense, France

[21] Appl. No.: 582,897

[22] PCT Filed: Apr. 17, 1989

[86] PCT No.: PCT/FR89/00172

§ 371 Date: Dec. 3, 1990

§ 102(e) Date: Dec. 3, 1990

[87] PCT Pub. No.: WO89/10371

PCT Pub. Date: Nov. 2, 1989

[30] Foreign Application Priority Data

Apr. 19, 1988 [FR] France .............................. 88 05178

[51] Int. Cl.$^5$ .............................................. C07F 9/09
[52] U.S. Cl. ...................................... 558/159; 558/157
[58] Field of Search ................................ 558/157, 159

[56] References Cited

U.S. PATENT DOCUMENTS 2,784,223  3/1957  Scalera et al. ...................... 562/556

FOREIGN PATENT DOCUMENTS 0237792  9/1987  European Pat. Off. ............. 562/556
1091317  4/1955  France ................................ 562/556

OTHER PUBLICATIONS

Orlov et al., Chemical Abstracts, vol. 83, No. 6, p. 3, No. 43805x, (1975).
Otsu et al., Makromol. Chem., Rapid Commun. 3, pp. 127–132 (1982).

Primary Examiner—James H. Reamer
Attorney, Agent, or Firm—Finnegan, Henderson, Farabow, Garrett and Dunner

[57] ABSTRACT

This compound (I) is prepared by reaction of a compound (II) with carbon disulphide in the presence of an oxidizing agent. It can be used as an agent performing the triple function of initiator, chain transfer agent and termination agent in the radical polymerization of vinyl monomers. The α,ω-difunctional vinyl oligomers and polymers thus obtained are fireproofing polymers or polymers which can be employed as additives in the preparation of fireproofing polymers. They can also be employed to manufacture block polymers by condensation of their end functional groups in the presence of at least one other functional oligomer or polymer, these block polymers also being fireproofing polymers.

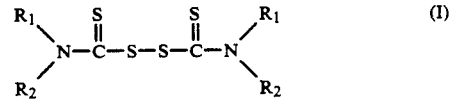

(I)

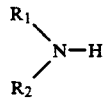

$R_1$, $R_2$ = especially $C_1$–$C_{12}$ alkyl optionally interrupted by —O— or,

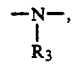

cycloalkyl, aryl, —Y—$R_4$ (Y = single bond, —O— or —$NR_5$); $R_4$ = phosphate or phosphonate functional group; at least one of $R_1$ and $R_2$ consisting of or carrying at least one phosphate or phosphonate functional group.

3 Claims, No Drawings

THIURAM DISULPHIDES CONTAINING PHOSPHATE OR PHOSPHONATE FUNCTIONAL GROUPS, THEIR PREPARATION AND THEIR USE IN THE MANUFACTURE OF FIREPROOFING VINYL POLYMERS

The present invention relates to new thiuram disulphides containing phosphate and phosphonate functional groups, to a process for the manufacture of these disulphides and to their use in the radical polymerization of vinyl monomers resulting in $\alpha, \omega$-difunctional vinyl oligomers and polymers.

The invention also relates to these $\alpha,\omega$-difunctional vinyl oligomers and polymers which, containing the phosphate and phosphonate functional groups originating from these thiuram disulphides, can be used as fireproofing polymers. Furthermore, these vinyl oligomers and polymers can also be used as additives in the manufacture of fireproofing polymers, and can also be used to manufacture block polymers by condensation with other functional oligomers or polymers, these block polymers also constituting fireproofing polymers.

Functional vinyl polymers, which are sought after because they can form part of the composition of polymers with specific properties, for example with fireproofing properties in the case of the invention, were hitherto generally prepared by the anionic route, using the reaction of active anions with suitable electrophiles. However, polymerization of this type is difficult to apply on an industrial scale. This is why, in recent years, radical polymerization techniques have been proposed, employing monofunctional and, in some cases, difunctional free-radical producing agents, such as the azo systems and the Redox systems. However, the functional groups in these systems are limited to the hydroxyl and carboxyl functional groups.

Nonfunctional tetraalkylthiuram disulphides have already been described by Takayuki Otsu et al in Makromol Chem. Rapid Commun. 127—132 (1982), as agents performing the triple function of initiator, chain transfer agent and termination agent in the radical polymerization of vinyl monomers, such agents being denoted in this paper by the abreviation "iniferter". Functional thiuram disulphides are proposed in European Patent Application EP-A-0,237,792 as iniferters. The functional groups envisaged do not include the phosphate or phosphonate functional groups (P functional groups).

The Applicant Company has now found that, when iniferters containing phosphate or phosphonate functional groups are employed, it is possible to obtain polymers with ends carrying P functional groups, which have a fire resistance superior to that of polymers carrying P functional groups along the chain.

The subject matter of the present invention is therefore a chemical compound denoted by the formula (I):

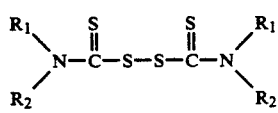

in which:
each of $R_1$ and $R_2$, independently of each other, denotes:

a linear or branched $C_1$-$C_{12}$, in particular $C_1$-$C_6$, alkyl group, optionally interrupted by —O— or

a $C_3$-$C_{12}$, in particular $C_5$-$C_7$, cycloalkyl group; an aryl group, for example a phenyl or naphthyl group;

a —Y—R. group, in which:
Y denotes a single bond, —O— or

and $R_4$ denotes a phosphate or phosphonate functional group;

$R_3$ and $R_5$ being chosen independently from the groups forming part of the definition of $R_1$ and $R_2$; it being possible for each of the groups $R_1$, $R_2$ and $R_3$ to carry at least one functional group chosen from the phosphate or phosphonate functional groups; on the condition that at least one of the radicals R and $R_2$ consists of or carries at least one phosphate or phosphonate functional group, it being possible for this functional group to be carried by the radical $R_3$ or $R_5$.

There may be mentioned, in particular:

the compounds of formula (I) in which each of $R_1$ and $R_2$ denotes a $C_1$-$C_6$ alkyl group, at least one out of these two groups carrying the phosphate or phosphonate functional group;

compounds of formula (I) in which $R_1$ (or $R_2$) denotes the group:

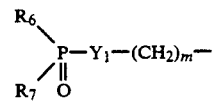

in which:
each of $R_6$ and $R_7$, which are identical or different, denotes an alkyl, alkoxy, aryl, aryloxy or

group, $R_8$ being chosen from the groups forming part of the definition of $R_1$ and $R_2$, it being possible for each of the groups $R_6$, $R_7$ and $R_8$ to be sustituted by at least one halogen atom; $Y_1$ denotes a single bond or —O— or else

$R_9$ being chosen from the groups forming part of the definition of $R_1$ and $R_2$; and
m ranges from 0 to 12, in particular from 2 to 6.

The compounds of formula (I) which have just been defined can be prepared by reaction of a compound of formula (II):

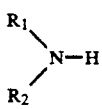

(II)

with carbon disulphide, in the presence of at least one oxidizing agent which is chosen, for example, from iodine, hydrogen peroxide, alkali metal hypochlorites and alkyl and aryl hydroperoxides.

In accordance with a first embodiment, a molar ratio of compound (II) to $CS_2$ which is substantially 2:1 is employed, according to the following presumed reaction scheme:

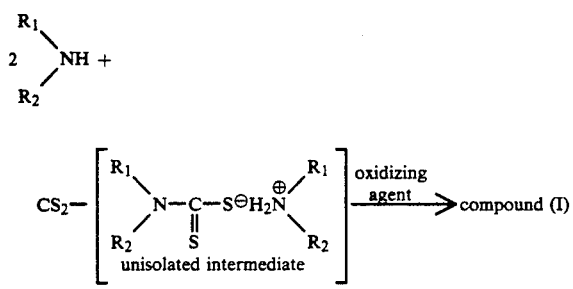

In accordance with a second embodiment, a molar ratio of compound (II) to $CS_2$: which is substantially 1:1 is employed, the reaction being carried out in the presence of a tertiary amine (for example pyridine or triethylamine), employed in a proportion of approximately mole per mole of compound (II) or of $CS_2$. In this case, the assumed reaction scheme is as follows:

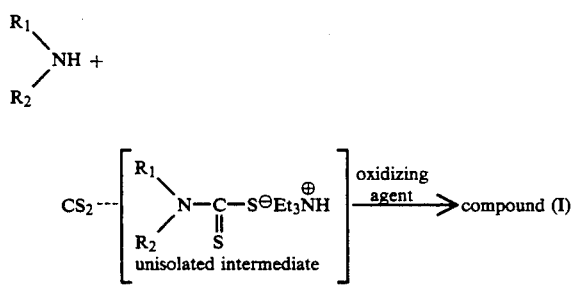

(the tertiary amine being $Et_3N$)

The reaction is exothermic and its exothermicity is controlled by any known means. Moreover, it is carried out in a solvent medium, it being possible for CS: itself to be used as a solvent.

Another subject of the present invention is the use of the compound of formula (I) as an iniferter agent in the radical polymerization of vinyl monomers, the said iniferter agent being introduced at the outset of polymerization with the mixture of monomers.

Vinyl monomers which may be mentioned are alkyl methacrylates and acrylates whose alkyl group contains, for example, from 1 to 8 carbon atoms, vinylaromatic hydrocarbons, unsaturated nitriles, lower alkoxy acrylates, cyanoethyl acrylate, acrylamide, lower hydroxyalkyl acrylates and methacrylates, acrylic acid and methacrylic acid, maleic anhydride and maleimides substituted by alkyl or aryl groups. There may be mentioned in particular methyl methacrylate, ethyl methacrylate, isopropyl methacrylate, n-butyl methacrylate, sec-butyl methacrylate, tert-butyl methacrylate, styrene, α-methylstyrene, monochlorostyrene, tert-butylstyrene, vinyl toluene and the like.

The general reaction scheme of this radical polymerization is as follows:

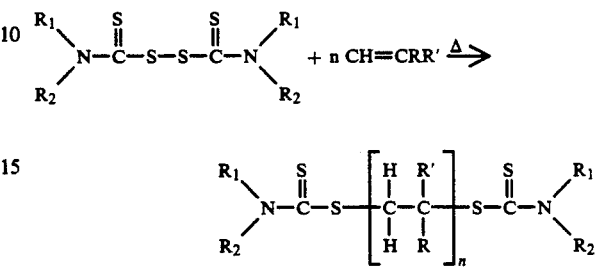

The quantity of iniferter which is introduced is generally between $0.1 \times 10^{-3}$ mol/l and 0.5 mol/l relative to the vinyl monomer. When the iniferter is incorporated in an excessively large quantity, the polymerization rate decreases, especially in the case of the acrylates, because it then acts chiefly as a termination agent for the primary radicals.

The stability of the

bonds of the polymer or of the oligomer obtained has been checked. Given that the iniferter carries phosphate or phosphonate functional groups, the resulting α,ω-difunctional oligomer or polymer then has a fireproofing nature, resulting in fireproofed materials, both when it is used by itself and in a mixture or in combination with other polymeric materials.

The invention also relates to the α, ω-difunctional difunctional vinyl oligomers and polymers obtained, such as defined above, to the use of these oligomers and polymers for manufacturing block polymers by condensation of their end functional groups in the presence of at least one other functional oligomer or polymer, and, finally, to the use of the vinyl oligomers and polymers such as defined above, as such, in the manufacture of fireproofed materials, as fireproofing polymers, as fireproofing additives or in the condensed state with at least one other functional oligomer or polymer.

It has been verified that the mechanical and physical properties of the resulting fireproofed materials are not affected appreciably by the presence of the fireproofing groups, and that these fireproofed materials exhibit a limiting oxygen index value (as measured according to ASTM standard D 2863-70) which is wholly acceptable.

To illustrate better the subject matter of the present invention a number of examples of embodiment thereof will be described below, these being given by way of guidance without any limitation being implied.

EXAMPLE 1

Synthesis of N,N'-dimethyl-N,N'-bis[2-(diethyl, N-methylphosphorylamido)ethyl]thiuram disulphide

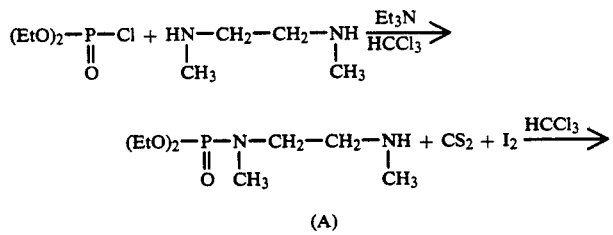

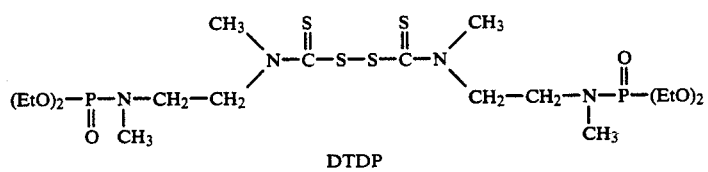

(A)

$$\begin{array}{c}
CH_3 \quad S \quad S \quad CH_3 \\
N-C-S-S-C-N \\
(EtO)_2-P-N-CH_2-CH_2 \quad\quad CH_2-CH_2-N-P-(EtO)_2 \\
\| \; | \quad\quad\quad\quad\quad\quad\quad\quad\quad\quad\quad\quad\quad | \; \| \\
O \; CH_3 \quad\quad\quad\quad\quad\quad\quad\quad\quad\quad\quad\quad CH_3 \; O
\end{array}$$

DTDP

Synthesis of the amine (A):

40 ml of dimethylethylenediamine (49.7 g; 0.56 moles) are dissolved in 150 ml of chloroform containing b 40 ml of triethylamine. 40 ml of diethyl chlorophosphate (47.8 g; 0.28 moles) dissolved in 125 ml of chloroform are added dropwise at ambient temperature over 2 hours. After the addition is completed the reaction mixture is kept stirred for 12 hours.

The solution is then washed with an aqueous sodium hydroxide solution (150 ml of $H_2O$ containing 15 g of NaOH) and then with distilled water (100 ml). The mixture is dried over $Na_2SO_4$. The solvent ($HCCl_3$) is then evaporated off under reduced pressure and the residue is distilled under vacuum. The fraction collected at 105° C./mm Hg corresponds to DTDP (42 % yield).

Characteristics:
1) colourless liquid
2) density: 1.05 g/ml
3) NH % : 6.7 %

Thiocarbamylation 20 g of the amine (A) (that is 0.09 moles) are dissolved in 100 ml of $CHCl_3$ containing 12.5 ml of triethylamine. 6.85 g (0.09 moles) of $CS_2$ are then added, together with 11.5 g of iodine. The mixture is stirred until the iodine has been completely consumed (colour change). The solution is then washed with 100 ml of distilled $H_2O$ 3 times in succession and is then dried over $Na_2SO_4$ for 48 hours. The solvent is evaporated off under reduced pressure at ambient temperature while being kept in the dark. A brown resin is obtained and is precipitated in petroleum ether (still in the dark). (Yield: 23 g, 85.6%).

| Elemental analysis (in %) | | | | | |
|---|---|---|---|---|---|
| C | H | N | O | P | S |
| 36.0 | 6.8 | 9.2 | 16.1 | 10.5 | 20.4 |

$^{31}P$ NMR ($CCl_4$) δppm 1.3 (triplet, 6H, $CH_3$—C—O)
2.7 (doublet, 3H, P—N—$CH_3$)
3.3 (3H, P—N—$CH_2$)

3.6 (singlet, 3H, C—N—$CH_3$)
              ‖
              S 4.0 (multiplet, 6H, O—$CH_2$ + C—N—$CH_2$)
                                ‖
                                S

EXAMPLES 2 to 9

Radical polymerization of methyl methacrylate and of styrene with the compound of Example 1 as iniferter Methyl methacrylate (Examples 2 to 4) and styrene (Examples 5 to 9) polymerizations were carried out according to the general operating procedure below, the polymerization temperature being set at 90° C in the case of Examples 2 to 4 and at 70° C in the case of Examples 5 to 9, and the initial concentration of iniferter and the polymerization time being varied.

General operating procedure:

$$CH_2=C\begin{matrix}CH_3\\COOMe\end{matrix} + DTDP \xrightarrow{\Delta}$$

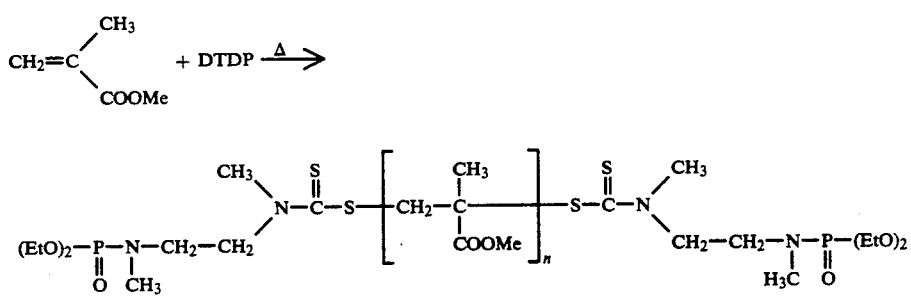

In the case of styrene, the polymer

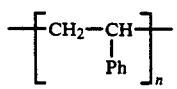

is obtained, capped at both ends by the same end groups as the poly(methyl methacrylate) above.

The polymerization is carried out in the absence of light, in evacuated and sealed 140×220 mm tubes immersed in an oil bath at a constant temperature. At the end of the the time shown the tubes are withdrawn, cooled in a dry ice-isopropanol mixture and the polymer is precipitated in methanol. The precipitate is collected in a sintered glass crucible, dried at 45° C overnight and weighed.

Methyl methacrylate polymerizations were carried out with an initial iniferter concentration of 0.06 moles/liter, the temperature and the polymerization time being varied. The number-average molecular mass of the polymer obtained was calculated in each case.

The results appear in Table I below:

TABLE I

| Polymer of Example | Initial DPTD concentration (moles/l) | Polymerization time (minutes) | Number-average molecular mass Mn |
|---|---|---|---|
| 2 | 0.06 | 170 | 25,000 |
| 3 | 0.13 | 900 | 17,200 |
| 4 | 0.25 | 900 | 10,000 |
| 5 | 0.02 | 220 | 28,100 |
| 6 | 0.03 | 220 | 22,100 |
| 7 | 0.16 | 1200 | 6,700 |
| 8 | 0.25 | 1200 | 4,700 |
| 9 | 0.30 | 1200 | 4,200 |

COMPARATIVE EXAMPLES 1 to 6

Copolymers of diethyl 2-(methacryloyloxy)ethyl phosphate (DMP) with methyl methacrylate (MMA) were prepared in solution in benzene (THF or DMF) by copolymerizing MMA with DMP in various proportions at 60° C. for between 1 and 2 hours in the presence of azobisisobutyronitrile (AIBN) as initiator, as described in J. Polym. Sci., Polym. Chem. 26, 1791 (1988).

The copolymers obtained were recovered by precipitation in diethyl ether.

COMPARATIVE EXAMPLES 7 to 12

Copolymers of 2-acryloyloxyethyl diethyl phosphate (ADP) with methyl methacrylate (MMA) were prepared in bulk at the same temperature and with the same initiator as the MMA-DMP copolymers of Comparative Examples 1 to 6, as described in Eur. Polym. J. 25, 251 (1989).

COMPARATIVE EXAMPLES 13 to 17

Copolymers of ADP with styrene were prepared as those of Comparative Examples 6 to 12, and as described in the publication Eur. Polym. J. 25, 251 (1989), with styrene replacing MMA in this case.

In the case of each of the polymers obtained in Examples 2 to 9 and in Comparative Examples 1 to 17, the percentage of phosphorus and the limiting oxygen index (LOI) values according to the ASTM standard 2863-70 of the polymers of these examples were measured (the percentage of oxygen/oxygen+ nitrogen which is necessary for the combustion to be sustained for 3 minutes is measured). The results are shown in Table II.

TABLE II

| | Examples | F(M)* | P % | LOI |
|---|---|---|---|---|
| Series I (Comp.) | Comp. 1 | 0.10 | 2.7 | 19 |
| | Comp. 2 | 0.25 | 5.3 | 20.5 |
| | Comp. 3 | 0.40 | 7.6 | 23 |
| | Comp. 4 | 0.55 | 8.9 | 24 |
| | Comp. 5 | 0.70 | 10 | 25 |
| | Comp. 6 | 0.80 | 10.6 | 28.5 |
| Series II (Comp.) | Comp. 7 | 0.10 | 1.4 | 22 |
| | Comp. 8 | 0.15 | 2.6 | 24 |
| | Comp. 9 | 0.30 | 3.5 | 25 |
| | Comp. 10 | 0.39 | 4.7 | 28 |
| | Comp. 11 | 0.31[b] | 5.0 | 30 |
| | Comp. 12 | 0.49 | 6.5 | 36 |
| Series III (Comp.) | Comp. 13 | 0.07 | 2.6 | 22 |
| | Comp. 14 | 0.11[a] | 4.0 | 23 |
| | Comp. 15 | 0.21 | 5.2 | 23.5 |
| | Comp. 16 | 0.30 | 6.5 | 25 |
| | Comp. 17 | 0.48 | 7.7 | 27 |
| Series IV (Inv.) | Ex. 2 | | 0.35 | 22.5 |
| | Ex. 3 | | 0.6 | 24 |
| | Ex. 4 | | 1.05 | 26.5 |
| Series V (Inv.) | Ex. 5 | | 0.22 | 22 |
| | Ex. 6 | | 0.47 | 26 |
| | Ex. 7 | | 0.93 | 29 |
| | Ex. 8 | | 1.33 | 29 |
| | Ex. 9 | | 1.48 | 32 |

*Molar fraction of the monomer in the MMA-comonomer or styrene-comonomer mixture.
[a] = reaction carried out at 45° C.
[b] = reaction carried out at 90° C.

The ratio $\Delta LOI/P$ was then calculated, $\alpha LOI$ being the LOI of the phosphonated polymer decreased by the LOI of the main chain, namely 17.5 in the case of PMMA and 20 in the case of polystyrene.

The curves of the $\Delta LOI$ values for all the types of polymers were plotted as a function of their phosphorus content using the least-square method for a first-order equation. The slope of the curves gives the apparent fireproofing efficiency of the particular phosphonated functional group on a comparative scale. The efficiency coefficients thus determined are given in Table III.

TABLE III

| Polymer type | I | II | III | IV | V |
|---|---|---|---|---|---|
| Efficiency coefficient | 0.85 | 2.66 | 0.96 | 5.81 | 7.30 |

When the main chain is PMMA the polymers of the invention have a fire behaviour from 2.2 to 6.8 times superior to that of the polymers of the Comparative Examples, the MMA-DMP copolymers having a $\alpha LOI/P$ ratio 6.8 times lower than the $\alpha, \omega$-difunctional PMMAs according to the invention, and the MMA-ADP copolymers have a $\Delta LOI/P$ ratio 2.2 times lower than the same polymers of the invention.

When the main chain is polystyrene the polymers of the invention have a $\Delta LOI/P$ ratio 7.6 times higher than that of the styrene-ADP copolymers.

We claim:

1. Chemical compound denoted by the formula (I):

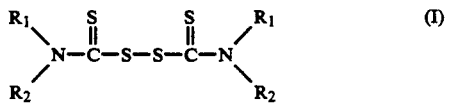

in which:

$R_1$ and $R_2$, independently of each other, denote:
   a linear or branched $C_1$-$C_{12}$ alkyl group, optionally interrupted by —O— or

a $C_3$-$C_{12}$ cycloalkyl group;
an aryl group;
a —Y—$R_4$ group, in which:
  Y denotes a single bond, —O— or

and
$R_4$ denotes a phosphate or phosphonate functional group;

$R_3$ and $R_5$ being chosen independently from the groups forming part of the definition of $R_1$, and $R_2$;

it being possible for each of the groups $R_1$, $R_2$ and $R_3$ to carry at least one functional group chosen from the phosphate or phosphonate functional groups, on the condition that at least one of the radicals either consists of or carries at least one phosphate or phosphonate functional group, it being possible for this functional group to be carried by the radical $R_3$ or $R_5$.

2. Compound according to claim 1, characterized in that the alkyl, cycloalkyl and phenyl groups forming part of the definition of $R_1$ and $R_2$ are, respectively, a $C_1$-$C_6$ alkyl group, a $C_5$-$C_7$ cycloalkyl group and a phenyl or naphthyl group.

3. Compound according to claim 1, characterized in that $R_1$ (or $R_2$) denotes the group:

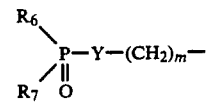

in which:
  each of $R_6$ and $R_7$, which are identical or different, denotes an alkyl, alkoxy, aryl, aryloxy or

group, $R_8$ being chosen from the groups forming part of the definition of $R_1$ and $R_2$, it being possible for each of the groups $R_6$, $R_7$ and $R_8$ to be substituted by at least one halogen atom; Y denotes a single bond or —O— or else

$R_9$ being chosen from the groups forming part of the definition of $R_1$ and $R_2$; and
m ranges from 0 to 12.

* * * * *